United States Patent

Parkins et al.

[11] Patent Number: 6,133,478
[45] Date of Patent: Oct. 17, 2000

[54] CATALYST AND PROCESS FOR PREPARING AMIDES

[76] Inventors: Adrian W Parkins, 2 Charlotte Place, 97 Wilton Road, London, United Kingdom, SW1V 1DP; Talit Ghaffar, 65 Valleyfield Road, Streatham, London, United Kingdom, SW16 2HS

[21] Appl. No.: 09/326,453

[22] Filed: Jun. 7, 1999

Related U.S. Application Data

[62] Division of application No. 08/913,255, Sep. 10, 1997, Pat. No. 5,932,756.

[30] Foreign Application Priority Data

Mar. 29, 1995 [GB] United Kingdom ............... 9506389

[51] Int. Cl.$^7$ .................................................. C07C 231/00
[52] U.S. Cl. .................. 564/126; 502/162; 502/439; 546/314; 546/316; 546/317; 556/14; 556/23; 564/128; 564/161; 564/204
[58] Field of Search ............... 556/14, 23; 502/162, 502/439; 564/126, 128, 204, 161; 546/316, 317, 314

[56] References Cited

U.S. PATENT DOCUMENTS 4,684,751  8/1987  Trogler et al. .................. 568/898
5,932,756  8/1999  Perkins et al. .................. 556/14

FOREIGN PATENT DOCUMENTS 0349087  1/1990  European Pat. Off. .

OTHER PUBLICATIONS

Tetrahedron Letters; vol. 36, No. 47, Nov. 20, 1995 pp. 8657–8660.

Inorganic Chemistry; vol. 14, No. 7, 1975 pp. 17321732–1734.

*Primary Examiner*—Shailendra Kumar
*Attorney, Agent, or Firm*—Bartlett & Sherer; Ronald B. Sherer

[57] ABSTRACT

A platinum complex useful as a catalyst for converting nitrites into amides comprises a platinum complex of dialkyl phosphine of stoichiometric formula: $PtX(R_2POHOPR_2)(PR_2OH)$ where R is an alkyl, alicyclic, chiral, alkylaryl group or substituted alkyl, alicyclic, chiral, alkaryl group or the two R groups attached to one phosphorous atom can form a heterocyclic ring with the phosphorous atom and X is H or a halide. The conversion takes place under reflux conditions to give a high yield of the amide.

16 Claims, No Drawings

CATALYST AND PROCESS FOR PREPARING AMIDES

This application is a Division of Parent application Ser. No. 08/913,255, filed Sep. 10, 1997, now U.S. Pat. No. 5,932,756.

The present invention relates to platinum phosphorus complexes and their use in a process for the hydration of nitrites to amides.

Amides such as acrylamide, acetamide and benzamide are important industrial chemicals and are used in a wide range of products. Other amides such as nicotinamide are also important as food supplements.

Known methods of making amides from nitrites include the sulphuric acid process in which acrylonitrile is hydrated using sulphuric acid at an elevated temperature and the acrylamide is then separated from the other products by the reaction of cooling.

Another method of preparing amides from nitrites is by the alkaline hydration of nitrites, optionally using a metal catalyst and this process is used to produce nicotinamide. These processes are briefly described in Ullmann's Encyclopaedia of Industrial Chemistry, 5th Edn: Vol. A1, Page 173 and in Kirk Othmer, Encyclopaedia of Chemical Technology, 3rd Edn: Vol 24, Page 67.

However, these processes, unless stringently controlled, can hydrolyse the amide to the acid and this has proved to be a difficulty in commercial operations.

To overcome this problem, enzymes have been used as catalysts, and industrially, heterogenous metal catalysts have been used, particularly to hydrolyse acrylonitrile to acrylamide.

A method of preparing amides and primary alcohols is also described in U.S. Pat. No. 4,684,751 using tertiary trialkyl phosphine complexes of platinum group metals, particularly the trimethyl phosphine complex.

In the process of this invention, nitrites are converted to the corresponding amide using, as a catalyst, a tertiary trimethyl phosphine complex of platinum in the presence of a nucleophile. However, this reaction only works effectively with some nitrites and the reaction needs to be carried out in an oxygen free atmosphere which makes it complex and difficult to operate industrially.

Methods for converting nitrites to amides using noble metal catalysts are also described in C M Jensen and W C Trogler, J Am Chem Soc 1986 108,723(1), G Villain, G Constant, A Gaset and P Kalck, J Mol, Cat. 1980 7,355(2) and T Yoshida, T Matsuda, T Okano, T Kitani and S Otsuka, J Am Chem Soc 1979 101,2027(3).

We have now discovered a class of platinum complexes of dialkyl and diaryl phosphine oxides which selectively convert nitrites to amides.

We have also discovered a method of making platinum complexes of the dialkylphosphine oxides of the invention.

According to the invention there is provided a platinum complex of dialkylphosphine of stoichiometric formula PtX$(R_2POHOPR_2)$ $(PR_2OH)$ where R is an alkyl, alicyclic, chiral, alkylaryl group or substituted alkyl, alicyclic, chiral, alkaryl group or the two R groups attached to one phosphorus atom can form a heterocyclic ring with the phosphorus atom and X is H or a halide such as chlorine or bromine.

The complexes of the invention are thought to have the structural formula

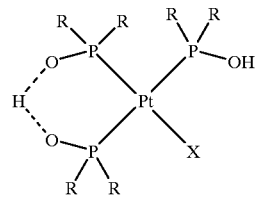

where R and X are as defined above.

In some cases the complex can be in an equilibrium mixture with its hydroxyl form, X=OH.

Preferably R is a $C_1$ to $C_5$ alkyl group and more preferably a methyl group.

According to the invention there is also provided a method of hydrating a nitrile to an amide which process comprises reacting the nitrile with water in the presence of the disubstituted phosphinite complex of platinum described above.

The platinum complexes of the present invention can be formed by different methods depending on the nature of X. E.g. when X=H by reacting a platinum triphenyl phosphine complex with a secondary phosphine oxide, $R_2P(O)H$, where R and X are as defined above. The reaction is thought to proceed according to the reaction mechanism:

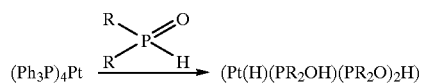

The reaction takes place preferably under normal conditions with regard to temperature and pressure and preferably is carried out in an inert organic solvent such as toluene; preferably the reaction is carried out under an inert atmosphere, e.g. nitrogen.

When X is a halogen by reacting a soluble platinum salt such as $K_2PtCl_4$ with a secondary phosphine oxide $R_2P(O)H$ according to the equation

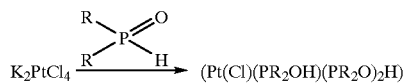

The reaction proceeds readily and gives a high yield of the desired end product.

By using as a starting material a mixture of substituted phosphinites where the R groups are different, a platinum complex can be obtained having a mixture of substituents.

We have now discovered that the platinum complexes of secondary phosphine oxides of the invention selectively convert nitrites to amides under normal conditions.

The reaction takes place by reacting the nitrile with the catalyst in aqueous solution at room temperature or with heating.

The platinum complex acts as a catalyst and is preferably present in a catalytic amount, e.g. from 0.001 to 1.0 mole per cent based on the weight of the nitrile, preferably 0.01 to 0.1 mole per cent.

The reaction can take place at normal temperature and pressure, although the reaction mixture can be heated to facilitate the reaction. The amount of water used in the reaction mixture is not critical and with the reduced tendency for the amide to hydrolyse to the acid excess water can be used.

For example, the hydrolysis reaction can take place by heating the nitrile with water in the presence of the platinum complex catalyst. If the nitrile is not water soluble an inert solvent such as ethanol or tetrahydrofuran can be added to form a solution.

The compounds where X is a halide, such as chlorine are not strongly active catalysts but reaction with a soluble silver salt, e.g. $AgBF_4$ converts these into the fully active form.

Alternatively the catalyst can be used as a heterogenous catalyst by supporting the catalyst on a suitable catalyst support. The catalyst supports which can be used include conventional catalyst supports such as silica, alumina, a silico-aluminate, a polymer or copolymer, such as a hydrocarbon polymer or copolymer e.g. a polystyrene polymer or copolymer.

Other phosphinito platinum complexes where X is a different atom or group can be converted into the catalysts of the present invention by replacement of the X moiety.

It is believed that the active catalyst consists of the cationic form and the invention comprises any compound which can give this form in solution. The cationic form is thought to have the structural formula:

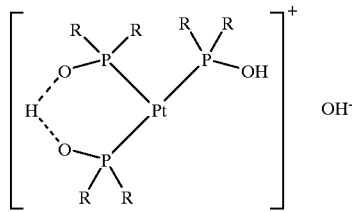

The invention can be used to prepare a range of amides, depending on the starting nitrile used, e.g. the invention can be used to convert acrylonitrile to acrylamide, acetonitrile to acetamide, benzonitrile to benzamide, 3-cyanopyridine to nicotinamide, halosubstituted aryl nitriles, e.g. di-fluorophenyl cyanide, to their corresponding amides which can be useful in biological applications such as drugs and biocides. Other nitrites which can be converted to their corresponding amides include polymers and copolymers containing nitrile groups and specific cyanides such as p-hydroxybenzylcyanide which can be converted to the corresponding amide which is used in the synthesis of Atenolol which is used as a β-blocker.

The invention will now be described in the following examples in which Examples 1–5 are examples of the preparation of the platinum catalyst.

PREPARATION OF CATALYSTS

EXAMPLE 1
Preparation of $[Pt(H)(PMe_2OH)(PMe_2O)_2H]$

Dimethyl phosphine oxide (0.16 g, 2.05 mmol) was added to a stirred solution of tetrakis (triphenyl phosphine) platinum (0) (0.5 g, 0.402 mmol) in dry toluene (10 ml) under nitrogen. Almost instantly a colourless solution was obtained which was stirred for one hour. During this time a white powder separated. Precipitation was completed by addition of ether (20 ml) and stirring for a further hour. The product was filtered off, washed with ether, hexane and dried under suction.

Yield: 0.13 g (75%)

The product was analysed and found to have the formula $[Pt(H)(PMe_2OH)(PMe_2O)_2H]$ EXAMPLE 2
Preparation of $[Pt(H)(PPh_2OH)(PPh_2O)_2H]$ Diphenyl phosphine oxide (0.45 g, 2.22 mmol) was added to a stirred solution of tetakis (triphenyl phosphine) platinum (0) (0.55 g, 0.44 mmol) in dry toluene 15 ml) under nitrogen. Almost instantly a pale yellow solution was obtained which was stirred for one hour. During this time a white powder separated. Precipitation was completed by addition of ether (25 ml) and stirring for a further hour. The product was filtered off, washed with ether, hexane and dried under suction.

Yield: 0.31 g (88%)

The product was analysed and found to have the formula $Pt(H)(PPh_2OH)(PPh_2O)_2H$ EXAMPLE 3
Preparation of $[PtCl(PMe_2OH)(PMe_2O)_2H]$ Dimethylphosphine oxide (0.17 g 2.18 mmol) in degassed ethanol (3 ml) was added dropwise over two hours to a stirred solution of $K_2PtCl_4$ (0.3 g 0.723 mmol) in degassed ethanol (9 ml) and $H_2O$ (5 ml). The reaction mixture was then stirred under nitrogen at 40–50° C. until it turned pale brown. Treatment with charcoal followed by filtration through celite gave a pale yellow solution which was concentrated under reduced pressure. Addition of water gave $[PtCl(PMe_2OH)(PMe_2O)_2H]$ (0.2 g, 60%) as fine white needles, which were washed with water, diethyl ether and dried in vacuo.

EXAMPLE 4
Preparation of $[PtCl(PMe_2Ph)(PMe_2O)_2H]$

A suspension of $[PtCl(PMe_2OH)(PMe_2O)_2H]$ (0.15 g, 0.324 mmol) in dry $CH_2Cl_2$ (20 ml) was treated with dimethylphenylphosphine (0.05 g, 0.362 mmol) and stirred at room temperature under nitrogen for an hour. The clear pale yellow solution was then concentrated under reduced pressure to ca 5 ml. Addition of diethyl ether/60–80 petroleum ether precipitated $[PtCl(PMe_2Ph)(PMe_2O)_2H]$ (0.14 g, 83%) as a white powder, which was filtered off, washed with diethyl ether and dried under suction.

EXAMPLE 5
Preparation of

Phospholane oxide (0.26 g, 2.50 mmol) in degassed ethanol (3 ml) was added dropwise over two hours to a stirred solution of $K_2PtCl_4$ (0.3 g, 0.723 mmol) in degassed ethanol (10 ml) and $H_2O$ (10 ml). The reaction mixture was then stirred under nitrogen at 40–50° C. for five hours. The resulting pale yellow solution was concentrated under reduced pressure to ca 5 ml. Addition of water gave [PtCl (PC₄H₈OH)(PC₄H₈O)₂H] (0.22 g, 56%) as a cream powder, which was washed with water, diethyl ether and dried in vacuo.

PREPARATION OF AMIDES

EXAMPLE 6
Preparation of Acetamide 0.0131 g (0.031 mmol) of the platinum complex prepared as Example 1, was stirred vigorously with 7.9 g (0.19 mol) of acetonitrile and 5 ml (0.28 mol) of water in a flask.

The resulting mixture was heated at 100° C. for 15 hours under reflux and allowed to cool. The cooled mixture was concentrated by evaporation under reduced pressure. A white powder was precipitated and was filtered from the liquid, dried in vacuo and weighed to give a yield of 10.2 grams. Analysis of this precipitate showed it to be acetamide and the yield was calculated at 90% on the weight of acetonitrile.

EXAMPLE 7
Preparation of Acrylamide 0.0096 g (0.022 mmol) of the catalyst of Example 1 was stirred vigorously with 8.1 g (0.15 mol) of acrylonitrile, 6 ml (0.33 mol) of water and 25 ml of ethanol in a flask and heated at 110° C. for 15 hours under reflux.

After cooling the liquids were removed using a rotary evaporator to give 10.12 grams of a white powder which, on analysis, was found to be acrylamide; the yield was calculated to be 94% based on the weight of acrylonitrile.

EXAMPLE 8
Preparation of Acrylamide

[PtCl(PMe₂OH)(PMe₂O)₂H] made as in Example 4 (0.0052 g, 0.0112 mmol) was dissolved in a vigorously stirred mixture of acrylonitrile (4.0 g, 0.076 mol), ethanol (4 ml) and water (3 ml, 0.166 mol). To this was added an excess of AgBF₄ (0.0062 g, 0.019 mmol) and the reaction mixture refluxed at 90° C. for three hours. After cooling, it was filtered to remove the precipitated AgCl. The solvent was then removed under reduced pressure to give acrylamide (4.50 g, 83%) which was dried in vacuo.

EXAMPLE 9
Preparation of Acetamide (0.010 g, 0.0216 mmol) of the catalyst prepared as in Example 4, was dissolved in a vigorously stirred mixture of acetonitrile (3.9 g, 0.096 mol) and water (3.5 ml, 0.194 mol). To this was added an excess of AgBF₄ (0.0057 g, 0.34 mmol) and the reaction mixture refluxed for three hours. After cooling, it was filtered to remove the precipitated AgCl. The solvent was then removed under reduced pressure to give acetamide (4.35 g, 77%), which was dried in vacuo.

EXAMPLE 10
Preparation of Acrylamide (0.0052 g, 0.0112 mmol) of the catalyst prepared as in Example 4, was dissolved in a vigorously stirred mixture of acrylonitrile (4.0 g, 0.076 mol), ethanol (4 ml) and water (3 ml, 0.166 mol). To this was added an excess of AgBF₄ (0.0062 g, 0.019 mmol) and the reaction mixture refluxed for three hours. After cooling, it was filtered to remove the precipitated AgCl. The solvent was then removed under reduced pressure to give acrylamide (4.50 g, 83%), which was dried in vacuo.

EXAMPLE 11
Preparation of Benzamide (0.0045 g, 0.0097 mmol) of the catalyst of Example 4, was dissolved in a vigorously stirred mixture of benzonitrile (3.5 g, 0.034 mmol), ethanol (7 cm³) and water (2 ml, 0.06 mmol). To this was added an excess of AgBF₄ (0.0045 g, 0.019 mmol) and the reaction mixture refluxed at 90° C. for five hours. After cooling, it was filtered to remove the precipitated AgCl. The solvent was then removed under reduced pressure to give benzamide (3.60 g, 87%), which was dried in vacuo.

TABLE 1

Catalytic Hydration of Various Nitriles using (PtH(PMe₂OH)(PMe₂O)₂}

| Nitrile | Product | Solvent | Turnover Rate mol/mol of cat.h) | Isolated Yield % |
| --- | --- | --- | --- | --- |
| H₂C=CHCN | H₂C=CHC)NH₂ | aqueous ethanol | 1485 | 93 |
| NC(CH₂)₄CN | H₂NCO(CH₂)₄CONH₂ | aqueous THF | 55 | 97 |
| C₆H₅-CN | C₆H₅-CONH₂ | aqueous ethanol | 518 | 86 |
| 3-pyridyl-CN | 3-pyridyl-CONH₂ | water | 450 | 91 |

TABLE 1-continued

Catalytic Hydration of Various Nitriles using {PtH(PMe₂OH)(PMe₂O)₂}

| Nitrile | Product | Solvent | Turnover Rate mol/mol of cat.h) | Isolated Yield % |
|---|---|---|---|---|
| 2,6-difluorobenzonitrile | 2,6-difluorobenzamide | aqueous THF | 220 | 73 |
| 1,2-dicyanobenzene | 2-cyanobenzamide | aqueous THF | 123 | 92 |
| 4-cyanobenzonitrile (terephthalonitrile) | 4-carbamoylbenzamide | aqueous THF | 173 | 96 |

\* Rate at which the diamide is produced

EXAMPLE 12
Preparation of Pyridine 4-Carboxamide (0.0051 g, 0.0119 mmol) of the platinum complex, prepared as in Example 1, was stirred with 4-cyanopyridine (2.0 g, 0.019 mol) and 0.75 ml (0.042 mol) of water and 10 ml tetrahydrofuran and the mixture heated under reflux for 4 hours. After cooling the liquids were removed using a rotary evaporator to give pyridine 4-carboxamide (2.12 g) corresponding to 90% yield.

EXAMPLE 13
Preparation of 4-Hydroxy Phenylacetamide (0.0032 g, 0.007 mmol) of the platinum complex, prepared as in Example 1, was stirred with 4-hydroxybenzyl cyanide (1.0 g, 7.5 mmol) and 5 ml (0.28 mol) of water and 5 ml ethanol and the mixture heated under reflux for 18 hours. After cooling the liquids were removed using a rotary evaporator to give 4-hydroxy phenylacetamide (1.116 g) corresponding to 98% yield.

EXAMPLES 14 TO 18

Various nitriles were hydrated to the corresponding amides using the process of Example 6 and the results shown in Table 1.

EXAMPLE 19

A comparison was made with other catalysts for the hydration of acetonitrile to acetamide and the results shown in the following Table 2.

TABLE 2

Comparison of the Catalytic Activities for the Hydration of Acetonitrile to Acetamide

| Catalyst | Temp. (° C.) | Turnover Frequency mol/(mol of cat. h) | Turnover Number mol/(mol of cat) | Ref |
|---|---|---|---|---|
| [PtH(PMe₂OH)(PMe₂O)₂H] | 90 | 380 | 5,700 | |
| [PtH(H₂O)(PMe₃)₂][OH] | 78 | 178 | 5,000–6,000 | (1) |
| [PtH(H₂O)(PEt₃)₂][OH] | 78 | 70 | not reported | (1) |
| PdCl(OH)(bipy)(H₂O) | 76 | 29 | not reported | (2) |
| Pt[P(C₆H₁₁)₃]₂ | 80 | 27 | 405 | (3) |
| Pt(PEt₃)₃ | 80 | 3 | 54 | (3) |
| NaOH | 78 | 0.4 | | |

The references refer to those on Page 1 of the specification. In the case of acrylonitrile, the turnover number was in excess of 50,000.

The selectivity of the catalyst of the invention is shown in Table 3 where various catalysts were used in the hydration of acrylonitrile and the amount of the unwanted alternative products β-cyanoethanol and β, β dicyano ethyl ether produced by 'hydration of the olefinic double bond in acrylonitrile determined. The superiority of the catalyst of the invention is the turnover frequency and/or selectivity is clearly seen.

TABLE 3

Catalytic Hydration of Acrylonitrile

| | Temp | Turnover frequency: mol/(mol of cat. h) | | | Selectivity for |
|---|---|---|---|---|---|
| | (° C.) | acrylamide | β-cyanoethanol | β,β-dicyanoethylether | Nitrile (%) |
| (PtH(PMe$_2$OH)(Me$_2$O)$_2$H) | 90 | 1485 | / | / | >99 |
| (PtH(H$_2$O)(PMe$_3$)$_2$(OH)) | 25 | 6.2 | 0.02 | 0.19 | 97 |
| (PtH(H$_2$O)(PMe$_3$)$_2$(OH)) | 80 | 65 | 84.5 | 10.5 | 29 |
| Pt(PPr'$_3$)$_3$ | 80 | 1.8 | 2.5 | 20.9 | 7.5 |
| (Pt(NHCOMe)(Ph)(PEt$_3$)$_2$) | 80 | 2.2 | 0.25 | 2.45 | 45 |

What is claimed is:

1. A method of forming an amide by reacting a nitrile with water in the presence of a catalyst which is a platinum complex of dialkylphosphine of stoichiometric formula PtX(R$_2$POHOPR$_2$) (PR$_2$OH) where R is a C$_1$ to C$_5$ alkyl group and X is H or a halide.

2. A method as claimed in claim 1 in which R is a methyl group.

3. A method as claimed in claim 1 in which X is bromine or chlorine.

4. A method of forming an amide by reacting a nitrile with water in the presence of a catalyst which is a platinum complex of dialkylphosphine which in solution forms a cation of the structural formula:

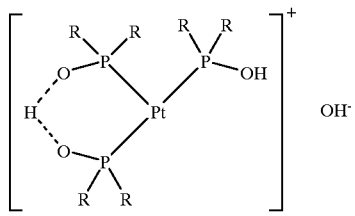

where R is C$_1$ to C$_5$ alkyl group.

5. A method of forming an amide by reacting a nitrile with water in the presence of a catalyst which is a platinum complex formed by reacting a platinum complex of stoichiometric formula PtX(R$_2$POHOPR$_2$) (PR$_2$OH) where R is a C$_1$ to C$_5$ alkyl group and where X is a halide, with a soluble silver salt.

6. A method of forming an amide by reacting a nitrile with water in the presence of a catalyst which is a platinum complex as claimed in claim 5 in which the soluble silver salt is AgBF$_4$.

7. A method of forming an amide as claimed in claim 1 in which the catalyst is on an inert catalyst support.

8. A method of forming an amide by reacting a nitrile with water in the presence of a catalyst composition as claimed in claim 1 in which the catalyst support comprises silica, alumina, a silico-aluminate, a polymer or copolymer or a polystyrene polymer or copolymer.

9. A method of forming an amide as claimed in claim 1 in which the reaction takes place by reacting the nitrile with the catalyst in aqueous solution at ambient temperature.

10. A method of forming an amide as claimed in claim 1 in which the catalyst is present in an amount of from 0.001 to 1.0 mole per cent based on the weight of the nitrile.

11. A method as claimed in claim 1 in which the nitrile is selected from acrylonitrile, acetonitrile, benzonitrile, 3-cyanopyridine, 4-cyanopyridine, 4-hydroxybenzyl cyanide, a halosubstituted aryl nitrile, or di-fluorophenyl cyanide.

12. A method of forming an amide as claimed in claim 4 in which the catalyst is on an inert catalyst support.

13. A method of forming an amide by reacting a nitrile with water in the presence of a catalyst composition as claimed in claim 4 in which the catalyst support comprises silica, alumina, a silico-aluminate, a polymer or copolymer or a polystyrene polymer or copolymer.

14. A method of forming an amide as claimed in claim 4 in which the reaction takes place by reacting the nitrile with the catalyst in aqueous solution at ambient temperature.

15. A method of forming an amide as claimed in claim 4 in which the catalyst is present in an amount of from 0.001 to 1.0 mole per cent based on the weight of the nitrile.

16. A method as claimed in claim 4 in which the nitrile is selected from acrylonitrile, acetonitrile, benzonitrile, 3-cyanopyridine, 4-cyanopyridine, 4-hydroxybenzyl cyanide, a halosubstituted aryl nitrile, or di-fluorophenyl cyanide.

* * * * *